United States Patent [19]
Otake et al.

[11] Patent Number: 5,942,427
[45] Date of Patent: Aug. 24, 1999

[54] N-ACETYLMANNOSAMINE DEHYDROGENASE GENE AND NOVEL RECOMBINANT DNA AS WELL AS A METHOD FOR PRODUCTION OF N-ACETYLMANNOSAMINE DEHYDROGENASE

[75] Inventors: Hideko Otake, Koshigaya; Yasuji Koyama, Noda; Tatsuo Horiuchi, Nagareyama; Eiichi Nakano, Iwatsuki, all of Japan

[73] Assignees: Noda Institute for Scientific Research; Kikkoman Corporation, both of Noda, Japan

[21] Appl. No.: 07/637,865

[22] Filed: Dec. 27, 1990

[30] Foreign Application Priority Data

Dec. 28, 1989 [JP] Japan .................................. 1-338267

[51] Int. Cl.$^6$ .............................. C12N 9/04; C12N 15/53; C12N 15/70
[52] U.S. Cl. ................... 435/190; 435/69.1; 435/252.33; 435/320.1; 536/23.7; 935/14; 935/29; 935/72; 935/73
[58] Field of Search ................................ 435/69.1, 320.1, 435/252.3, 190, 252.33; 536/27, 23.7

[56] References Cited

U.S. PATENT DOCUMENTS

| | | | |
|---|---|---|---|
| 4,721,671 | 1/1988 | Anilionis et al. | 435/68 |
| 4,768,592 | 9/1988 | Deal et al. | 435/7 |
| 4,788,135 | 11/1988 | Davis et al. | 435/6 |
| 4,960,701 | 10/1990 | Horiuchi et al. | |
| 5,021,342 | 6/1991 | Greene et al. | 435/91 |
| 5,026,636 | 6/1991 | Baseman et al. | 435/6 |
| 5,104,973 | 4/1992 | Kondo et al. | 530/334 |
| 5,110,908 | 5/1992 | Deich et al. | 530/403 |

OTHER PUBLICATIONS

Garrels, J.I., 1979, The Journal of Biological Chemistry, 254(16): 7961–7977.
Doye, V., et al., 1989, The Journal of Biological Chemistry, 264(21): 12134–12137.
Sobel, A., et al., 1989, The Journal of Biological Chemistry, 264(7): 3765–3772.
Oda, M., et al., 1985, Journal of General and Applied Microbiology, 31: 93–105.
Amann, R., et al., 1988, FEMS Microbiology Letters, 50: 101–106.
Kita, K., et al., 1989, Nucleic Acids Research 17(21): 8741–8753.
Kemp, D.J., et al., 1981, Proceedings of the National Academy of Sciences, USA, 78(7): 4520–4524.
Young, R.A., et al., 1983, Science 222: 778–782.
Saggs, S.V., et al., 1981, Proceedings of the National Academy of Sciences, USA 78(11): 6613–6617.
Hewick, R. M., et al, 1981, The Journal of Biological Chemistry 256(15): 7990–7997.
Newland, J. W., et al., 1988, Journal of Clinical Microbiology 26(7): 1292–1297.
Matsuda, G., et al., 1981, FEBS Letters, 126(1): 111–113.

*Primary Examiner*—Robert A. Wax
*Assistant Examiner*—William W. Moore
*Attorney, Agent, or Firm*—Banner & Witcoff, Ltd.

[57] ABSTRACT

N-acetylmannosamine dehydrogenase gene derived from a microorganism belonging to the genus Flavobacterium, e.g., Flavobacterium sp. No. 141-8 strain and defined by a specific restriction enzyme map which encodes 271 amino acid sequence. Using the recombinant DNA, N-acetylmannosamine dehydrogenase can be produced in a simpler manner in an industrial scale. The enzyme is useful for quantitative determination of sialic acid.

4 Claims, 3 Drawing Sheets

```
                                            10                                        20
Met Thr Thr Ala Gly Val Ser Arg Arg Pro Gly Arg Leu Ala Gly Lys Ala Ala Ile Val
                                            30                                        40
Thr Gly Ala Ala Gly Gly Ile Gly Arg Ala Thr Val Glu Ala Tyr Leu Arg Glu Gly Ala
                                            50                                        60
Ser Val Val Ala Met Asp Leu Ala Pro Arg Leu Ala Ala Thr Arg Tyr Glu Glu Pro Gly
                                            70                                        80
Ala Ile Pro Ile Ala Cys Asp Leu Ala Asp Arg Ala Ala Ile Asp Ala Ala Met Ala Asp
                                            90                                       100
Ala Val Ala Arg Leu Gly Gly Leu Asp Ile Leu Val Ala Gly Gly Ala Leu Lys Gly Gly
                                           110                                       120
Thr Gly Asn Phe Leu Asp Leu Ser Asp Ala Asp Trp Asp Arg Tyr Val Asp Val Asn Met
                                           130                                       140
Thr Gly Thr Phe Leu Thr Cys Arg Ala Gly Ala Arg Ala Met Val Ala Ala Gly Ala Gly
                                           150                                       160
Lys Asp Gly Arg Ser Ala Arg Ile Ile Thr Ile Gly Ser Val Asn Ser Phe Met Ala Glu
                                           170                                       180
Pro Glu Ala Ala Ala Tyr Val Ala Ala Lys Gly Gly Val Ala Met Leu Thr Arg Ala Met
                                           190                                       200
Ala Val Asp Leu Ala Arg His Gly Ile Leu Val Asn Met Ile Ala Pro Gly Pro Val Asp
                                           210                                       220
Val Thr Gly Asn Asn Thr Gly Tyr Ser Glu Pro Arg Leu Ala Glu Gln Val Leu Asp Glu
                                           230                                       240
Val Ala Leu Gly Arg Pro Gly Leu Pro Glu Glu Val Ala Thr Ala Ala Val Phe Leu Ala
                                           250                                       260
Glu Asp Gly Ser Ser Phe Ile Thr Gly Ser Thr Ile Thr Ile Asp Gly Gly Leu Ser Ala
                                           270
Met Ile Phe Gly Gly Met Arg Glu Gly Arg Arg
```

FIG. 3

```
ATG ACG ACA GCA GGC GTT TCG AGG CGG CCC GGA CGG CTT GCG GGC AAG GCG GCG ATC GTC
                                30                                              60
ACC GGC GCC GGC GGC ATC GGC GCC CGC GCC ACC GTC GCC GAG GCC TAT CTT CGC GAG GGC GCC
                                90                                              120
AGC GTG GCG GCG ATG GAC CTC GCG CCG CGC CTC GCC GCC ACC CGC GCC TAT GAG GAA CCC GGC
                                150                                             180
GCC ATC CCG ATC GCC TGC CTT GCC GAC CGC GAC GCG GCG ATC GAC GCG ATG GCC GAC
                                210                                             240
GCG GTC GCC CTC GGG CTG GAC GGG CTG ATT CTC GTC GCC GGC GCG CTC AAG GGC GGG
                                270                                             300
ACC GGC AAT TTC CTC GAT CTC TCC GAC GCC TGG GAC CGC TAT GTC GAC GTC AAC ATG
                                330                                             360
ACC GGC ACC TTC CTC ACC TGC CGC GCC ATC ATC GGC GCC GCC ATG GTG GCG GCC GCC GGC
                                390                                             420
AAG GAC GGC CGG TCC GCG CGC ATC GGC GCC TCC GTC AAT TCC TTC ATG GCC GCC GAG
                                450                                             480
CCG GAG GCG GCC GCC TAT GTC GCG GGC GCC ATG CTG ACC CGC GCC GTC GCC ATG
                                510                                             540
GCC GTC GAC CTC GCC CGC CAC GGC ATC GTC AAC ATG ATT GCC CCC GGC CAG GTC CCC GTC GAC
                                570                                             600
GTG ACC GGC AAC AAC ACC GGC TAC AGC CGG GAA CCG CGC CTC GCG GCC ACC GCG GAC GAG
                                630                                             660
GTG GCG CTG GGC AGG CCC GGC CTG CCG GAG GAA GTG CCG ACC GCG GTC GTG TTC CTG GCC
                                690                                             720
GAG GAC GGG TCG AGC TTC ATC ACC GGC ACG ATC ACC ATC GAC GGC GGC CTC TCC GCC
                                750                                             780
ATG ATC TTC GGC ATG CGG GAA GGC CGA CGC TGA
                                810
```

FIG. 4

```
Met Thr Thr Ala Gly Val Ser Arg Arg Pro Gly Arg Leu Ala Gly Lys Ala Ala Ile Val      20
Thr Gly Ala Ala Gly Gly Ile Gly Arg Ala Thr Val Glu Ala Tyr Leu Arg Glu Gly Ala      40
Ser Val Val Ala Met Asp Leu Ala Pro Arg Leu Ala Ala Thr Arg Tyr Glu Glu Pro Gly      60
Ala Ile Pro Ile Ala Cys Asp Leu Ala Asp Arg Ala Ala Ile Asp Ala Ala Met Ala Asp      80
Ala Val Ala Arg Leu Gly Gly Leu Asp Ile Leu Val Ala Gly Gly Ala Leu Lys Gly Gly     100
Thr Gly Asn Phe Leu Asp Leu Ser Asp Ala Asp Trp Asp Arg Tyr Val Asp Val Asn Met     120
Thr Gly Thr Phe Leu Thr Cys Arg Ala Ala Ala Arg Ala Met Val Ala Ala Gly Ala Gly     140
Lys Asp Gly Arg Ser Ala Arg Ile Ile Thr Ile Gly Ser Val Asn Ser Phe Met Ala Glu     160
Pro Glu Ala Ala Tyr Val Ala Ala Lys Gly Gly Val Ala Met Leu Thr Arg Ala Met         180
Ala Val Asp Leu Ala Arg His Gly Ile Leu Val Asn Met Ile Ala Pro Gly Pro Val Asp     200
Val Thr Gly Asn Asn Thr Gly Tyr Ser Glu Pro Arg Leu Ala Glu Gln Val Leu Asp Glu     220
Val Ala Leu Gly Arg Pro Gly Leu Pro Glu Glu Gln Val Ala Ala Thr Ala Val Phe Leu Ala  240
Glu Asp Gly Ser Ser Phe Ile Thr Gly Ser Thr Ile Thr Ile Asp Gly Gly Leu Ser Ala     260
Met Ile Phe Gly Gly Met Arg Glu Gly Arg Arg                                          270
```

N-ACETYLMANNOSAMINE DEHYDROGENASE GENE AND NOVEL RECOMBINANT DNA AS WELL AS A METHOD FOR PRODUCTION OF N-ACETYLMANNOSAMINE DEHYDROGENASE

FIELD OF THE INVENTION

The present invention relates to N-acetylmannosamine dehydrogenase gene and novel recombinant DNA as well as a method for production of N-acetylmannosamine dehydrogenase.

RELATED ART

The present inventors previously made investigations on a method for determination of sialic acid in a simple fashion with high accuracy and found that bacteria belonging to the genus Flavobacterium which had been isolated from soil acted on N-acetylmannosamine to produce N-acetylmannosamine lactone and at the same time, produce a novel enzyme capable of reducing NAD to NADH and this enzyme could be effectively utilized for determination of sialic acid, and filed a patent application directed to N-acetylmannosamine dehydrogenase and a process for preparation thereof, which issued as U.S. Pat. No. 4,960,701 on Oct. 2, 1990.

A structure of the N-acetylmannosamine dehydrogenase gene derived from bacteria belonging to the genus Flavobacterium, for example, Flavobacterium sp. No. 141-8 strain is quite unknown. It is the actual situation that the gene has not been even isolated.

On the other hand, when this N-acetylmannosamine dehydrogenase is used, quantitative assay of N-acetylmannosamine can be made with good accuracy and an amount of sialic acid can be assayed based on N-acetylmannosamine. As the result, diagnosis of various diseases can be efficiently made. However, various restrictions are involved in producing N-acetylmannosamine dehydrogenase in an industrial scale. It is currently desired to eliminate these restrictions. That is, it is mandatorily required for the above process of producing N-acetylmannosamine dehydrogenase to add expensive N-acetylmannosamine or N-acetylglucosamine as an inducer into medium. In this regard, the process supra is thus disadvantageous from an economical viewpoint. In addition, the strain grows slowly so that a long period for incubation is required, techniques such as jar incubation, etc. involving limitations to practice in an industrial scale are necessary to obtain a high yield, its purification steps are complicated, etc. Therefore, the process also involves complicated operations. For these reasons, the process encounters a drawback that yield of the enzyme is seriously reduced sometimes.

SUMMARY OF THE INVENTION

The present inventors have made various studies on N-acetylmannosamine dehydrogenase gene derived from bacteria belonging to the genus Flavobacterium, for example, Flavobacterium sp. No. 141-8 strain, and as a result, have isolated the gene for the first time. Subsequent investigations on efficient production of N-acetylmannosamine dehydrogenase using the gene described above have led to the finding that by incubating in medium Escherichia coli transformed with recombinant DNA, which is obtained by incorporating a gene of the enzyme derived from Flavobacterium, for example, Flavobacterium sp. No. 141-8 strain, into vector DNA, e.g., plasmid vector DNA, the enzyme can be efficiently produced in the cells of the bacteria, without supplementing the aforesaid expensive additive to the medium. The present invention has thus been completed.

That is, one aspect of the present invention lies in an N-acetylmannosamine dehydrogenase gene derived from a microorganism belonging to the genus Flavobacterium and defined by the following restriction enzyme cleavage map:

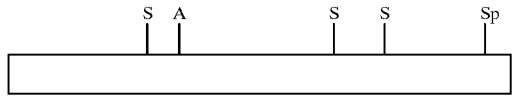

(wherein S is Sal I, A is Aat II and Sp is Sph I). The gene in accordance with the present invention is N-acetylmannosamine dehydrogenase gene encoding an amino acid sequence which has 271 amino acids shown by SEQ ID NO:2 and starts with methionine.

Another aspect of the present invention lies in novel recombinant DNA characterized by incorporating an N-acetylmannosamine dehydrogenase gene derived from a microorganism belonging to the genus Flavobacterium and defined by the following restriction enzyme cleavage map:

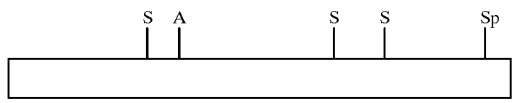

(wherein S is Sal I, A is Aat II and Sp is Sph I), into vector DNA. That is, the present invention is directed to novel recombinant DNA obtained by incorporating into vector DNA an N-acetylmannosamine dehydrogenase gene encoding an amino acid sequence which has the 271 amino acids shown by SEQ ID NO:2 and starts with methionine.

A further aspect of the present invention lies in a method for production of N-acetylmannosamine dehydrogenase which comprises culturing in medium a microorganism belonging to the genus Escherichia, which has been transformed with novel recombinant DNA obtained by incorporating N-acetylmannosamine dehydrogenase gene derived from a microorganism belonging to the genus Flavobacterium and defined by the following restriction enzyme cleavage map:

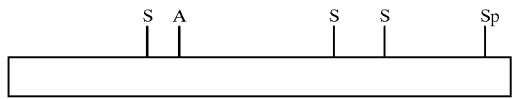

(wherein S is Sal I, A is Aat II and Sp is Sph I) into vector DNA, and collecting N-acetylmannosamine dehydrogenase from the culture. That is, the present invention is directed to a method for production of N-acetylmannosamine dehydrogenase which comprises culturing in medium a microorganism belonging to the genus Escherichia, which has been transformed with novel recombinant DNA obtained by incorporating an N-acetylmannosamine dehydrogenase gene encoding an amino acid sequence, which has 271 amino acids as shown by SEQ ID NO:2 and starts with methionine, into vector DNA, and collecting N-acetylmannosamine dehydrogenase from the culture.

BRIEF DESCRIPTION OF THE DRAWINGS

FIG. 3 shows the entire nucleotide sequence (SEQ ID NO:1) of N-acetylmannosamine dehydrogenase gene. FIG. 4 shows the amino acid sequence (SEQ ID NO:2) of polypeptide translated from the N-acetylmannosamine dehydrogenase gene.

DETAILED DESCRIPTION OF THE INVENTION

Figure 2:
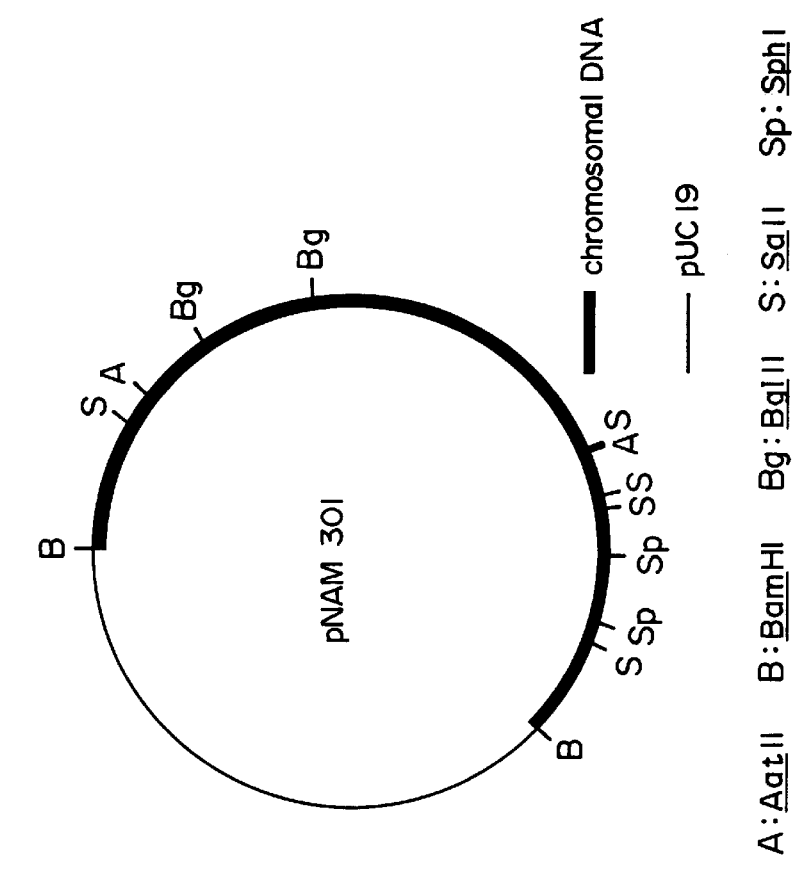
FIG. 2 shows a restriction enzyme cleavage map of recombinant plasmid pNAM 301 DNA.

Hereinafter the present invention is described in detail.

Turning firstly to bacteria belonging to the genus Flavobacterium which are used as donors of the N-acetylmannosamine dehydrogenase gene in the present invention, there are, for example, Flavobacterium sp. No. 141-8 strain (FERM BP-1222), etc.

Then, the microorganism described above is cultured in quite the same manner as described in U.S. Pat. No. 4,960, 701, issued Oct. 2, 1990, to obtain the culture. The cells of, e.g., Flavobacterium sp. No. 141-8 strain, are obtained from the culture in a conventional manner, for example, by filtration, centrifugation, etc.

From the cells, chromosomal DNA can be obtained by a method described in, e.g., Current Protocols in Molecular Biology, Unit 2.4.3. (John Wiley & Sons, Inc., 1987) or the like.

Next, the thus obtained chromosomal DNA is incorporated into the phage vector λgt11 using, e.g., cDNA Cloning System manufactured by Amersham Co., Ltd. to obtain various recombinant phages. *E. coli* Y-1090 to obtain plaques is infected with the phage capable of producing various fused proteins.

In order to detect the plaques which produce fused protein with N-acetylmannosamine dehydrogenase (namely, recombinant phage containing an N-acetylmannosamine dehydrogenase gene fraction), the method may be applied as described in brochure (section 5, page 8) by Promega Biotec Co., Ltd., 2800 S. Fish Hatchery Road, Madison, Wis. 53711, USA, which states: "Fusion protein expression, though normally repressed, is inducible by exposing the growing bacteriophage or lysogens to IGPT (isopropyl β-D thiogalactopyranoside."

For purification of phage DNA from the thus obtained recombinant phage, the technique described in Molecular Cloning, pages 371 and 372, Cold Spring Harbor Laboratory (1982) may be used.

Then, incomplete N-acetylmannosamine dehydrogenase gene DNA is labeled with, e.g., [α-$P^{32}$] dCTP (purchased from Amersham Japan) by Random Primer Extension Labeling System [manufactured by Du Pont Inc.] or the like. Using the DNA as a probe, a DNA fraction containing complete N-acetylmannosamine dehydrogenase gene can be obtained from chromosomal DNA library prepared using phage vector EMBL 3 [manufactured by STRATAGENE Co., Ltd.] as a vector, in accordance with plaque hybridization [Current Protocols in Molecular Biology].

The thus obtained DNA fragment is subjected to, e.g., ordinary agarose gel electrophoresis, which is further purified by means of purification, e.g., extraction with phenol, etc. and concentrated by means of concentration such as ethanol precipitation, etc. Thus, a DNA fragment containing purified N-acetylmannosamine dehydrogenase gene (SEQ ID NO:1) can be obtained.

As vector DNA which can be used in the recombinant DNA of the present invention, any vector DNA can be used. There are, for example, plasmid vector DNA, bacteriophage vector DNA, etc. More specifically, plasmid pUC19 DNA (manufactured by Takara Shuzo Co., Ltd., or the like is preferred.

The vector DNA described above is digested with a restriction enzyme for causing staggered end, for example, BamH I (manufactured by Takara Shuzo Co., Ltd.) at a temperature above 30° C., preferably 37° C. in an enzyme concentration of 10 to 1000 units/ml for at least an hour, preferably 1 to 3 hours to give cleaved vector DNA.

Then, the thus obtained DNA fragment derived from the genus Flavobacterium, e.g., Flavobacterium sp. No. 141-8 strain and containing N-acetylmannosamine dehydrogenase gene is mixed with the cleaved vector DNA. *E. coli* DNA ligase (manufactured by New England Biolabs Co., Ltd.), T4 DNA ligase (manufactured by Boehringer Mannheim Co.), etc., preferably T4 DNA ligase then acts on the mixture at a temperature of 4 to 37° C., preferably 4 to 16° C. in an enzyme concentration of 1 to 100 units/ml for an hour or longer, preferably 6 to 24 hours to give recombinant DNA. The thus obtained recombinant DNA is then digested with restriction enzymes for causing staggered end, for example, Pst I and Xba I (both manufactured by Takara Shuzo Co., Ltd.) at a temperature above 30° C., preferably 37° C. in an enzyme concentration of 10 to 100 units/ml for at least an hour, preferably 1 to 3 hours. Then, DNA is deleted using deletion kit for kilo sequencing (manufactured by Takara Shuzo Co., Ltd.) to give recombinant DNA having a further limited region containing the complete N-acetylmannosamine dehydrogenase gene.

Using this recombinant DNA, for example, *E. coli* K-12, preferably *E. coli* JM 109 (acquired from Takara Shuzo Co., Ltd.), E. coli HB 101 (ATCC 33694), E. coli DHI (ATCC 33849), *E. coli* X-1776 (ATCC 31244), and the like, are transformed or transduced to give the respective recombinant strains. The transformation may be performed according to the method of D. M. Morrison [Methods in Enzymology, 68, 326–331 (1979)]. The transduction may be performed according to the method of B. Hohn [Methods in Enzymology, 68, 299–309 (1979)].

From the recombinant strains described above, a strain capable of producing N-acetylmannosamine dehydrogenase is attained by screened procedures briefly described in the table below. Thus, a strain which bears recombinant DNA obtained by incorporating the N-acetylmannosamine dehydrogenase gene-containing DNA into vector DNA, is capable of producing N-acetylmannosamine dehydrogenase and belongs to the genus Escherichia can be obtained.

TABLE I

| Shake culture of the recombinant strain in 1 ml of T-Y medium supplemented with 1 mM IPTG at 37° C. for 16 hours Centrifugation (8000 rpm, 10 minutes) Addition of 1 ml of 0.1 M Tris-HCl buffer, pH 8.2 (standard buffer) containing 0.5% Triton X-100 to the cells Ultrasonic homogenization (3 minutes) to give crude enzyme solution | |
|---|---|
| Crude enzyme solution | 150 μl |
| 4% NAD | 50 μl |
| 0.35 M NAM | 50 μl |
| PMS-NBT mixture | 50 μl |
| A strain which was stained to blue with the following composition was selected: | |
| PMS (phenazine methosulfate, Wako Pure Chemicals) | 1 mg |
| NBT (nitro blue tetrazolium, Wako Pure Chemicals) | 10 mg |
| $H_2O$ | 10 ml |

The novel purified recombinant DNA may be collected from the thus obtained strain by, e.g., the method of P.

Guerry et al. [J. Bacteriology, 116, 1064–1066 (1973)], the method of D. B. Clewell [J. Bacteriology, 110, 667–676 (1972)], etc.

Using the aforesaid DNA containing N-acetylmannosamine dehydrogenase gene, determination of the entire nucleotide sequence (SEQ ID NO:1) of the N-acetylmannosamine dehydrogenase gene alone was performed by the procedure as shown in Example, Step (6). Then, the amino acid sequence (SEQ ID NO:2) of the polypeptide translated by the gene having the nucleotide sequence is established.

The gene encoding the thus established amino acid sequence (SEQ ID NO:2) is the N-acetylmannosamine dehydrogenase gene of the present invention.

Next, N-acetylmannosamine dehydrogenase is produced by culturing the thus obtained strain containing the recombinant DNA obtained by incorporating the N-acetylmannosamine dehydrogenase gene-containing DNA into vector DNA, capable of producing N-acetylmannosamine dehydrogenase and belonging to the genus Escherichia to obtain the culture, as described below.

The microorganism described above may be cultured by conventional solid incubation but it is preferred to adopt liquid incubation, since rapid growth can be achieved.

As the medium for incubation of the microorganism, any medium for incubation of E. coli is usable. In general, however, there is used a medium containing at least one nitrogen source of yeast extract, peptone, meat extract, and corn steep liquor or soybean or wheat bran extract, which is supplemented with at least one inorganic salt such as potassium primary phosphate, potassium secondary phosphate, magnesium sulfate, sodium chloride, magnesium chloride, ferric chloride, ferric sulfate, manganese sulfate, etc.; and if necessary and desired, further appropriately supplemented with glucid materials, vitamins, etc. If necessary, isopropyl-β-D-thiogalactoside (hereafter abbreviated as IPTG) may also be added.

It is appropriate to control initial pH of the medium to a range of 7 to 9. It is desired to perform incubation at 30 to 42° C., preferably at about 37° C., for 4 to 24 hours, preferably 6 to 24 hours by aerial spinner deep culture, shake culture, stationary culture, etc.

After completion of the incubation, N-acetylmannosamine dehydrogenase is collected, isolated and purified from the culture according to exactly the same manner as described in U.S. Pat. No. 4,960,701, issued Oct. 2, 1990. In general, however, column chromatography on DEAE cellulose, column chromatography using phenyl Sepharose or gel filtration by Sephadex give the enzyme in a high purity. Purification is also advantageous because several steps can be omitted, as compared to the case of using bacteria belonging to the genus Flavobacterium.

The thus obtained N-acetylmannosamine dehydrogenase has physicochemical properties similar to the enzyme described in U.S. Pat. No. 4,966,701, with specific activity being higher by about 1.5 times.

By culturing the strain containing the recombinant DNA having incorporated therein the N-acetylmannosamine dehydrogenase gene of the present invention and belonging to the genus Escherichia, N-acetylmannosamine dehydrogenase can be efficiently obtained, without using any medium supplemented with expensive N-acetylmannosamine, N-acetylglucosamine, etc. which are known to be inducers of dehydrogenase. Therefore, the present invention is extremely useful from an industrial point of view.

[EXAMPLES]

The present invention is described more specifically with reference to the examples.

(1) Preparation of chromosomal DNA

Flavobacterium sp. No. 141-8 strain (FERM BP-1222) was inoculated on 1 liter of medium [0.75% glucose, 0.2% Bacto Yeast Extract (manufactured by Difco Co.), 0.9% Nutrient Broth (manufactured by Difco Co.) and 0.1% $KH_2PO_4$ (pH 8.0)], which was shake cultured at a temperature of 30° C. for 2 days to give the culture. After the culture was centrifuged at 8,000 rpm for 10 minutes, 90 μg of chromosomal DNA was extracted from the culture by the method described in Current Protocols in Molecular Biology, unit 2.4.3. (John Wiley & Sons, Inc., 1987).

(2) Preparation of recombinant bacteriophage λgtll-NAM 6 DNA

After 90 μg of the chromosomal DNA obtained in STEP (1) and 2 units each of restriction enzymes Acc I, Alu I and Hae III (all manufactured by Takara Shuzo Co., Ltd.) were mixed with Tris-HCl buffer (pH 7.5) containing 10 mM $MgCl_2$ and 1 mM dithiothreitol (hereafter abbreviated as L-buffer), respectively, the mixture was reacted at a temperature of 37° C. for 30 minutes. After the reaction was completed, the reaction mixture was subjected to 0.7% (W/V) agarose gel (manufactured by Takara Shuzo Co., Ltd.) electrophoresis. A DNA fragment having a size of 0.5 to 2.5 kb was then eluted according to the method of R.C.A. Yang et al. [Methods in Enzymology, 68, 176–182 (1979)] to give eluate. The eluate was extracted with phenol and precipitated with ethanol in a conventional manner to give 15 μg of chromosomal DNA fragment of Flavobacterium sp. No. 141-8 strain digested with Acc I, Alu I and Hae III.

The DNA fragment, 15 μg, thus obtained was ligated with phage vector λgtll arm DNA according to "CDNA Cloning System" λgtll manufactured by Amersham Co., Ltd.

Then, the DNA was enclosed with enveloped protein of bacteriophage by the in vitro packaging method to prepare bacteriophage particles. The bacteriophage particles thus obtained were inoculated on T-Y agar medium [1% Trypton (manufactured by Difco Co.), 0.5% yeast extract (manufactured by Difco Co.), 0.5% NaCl and 1.2% agar] containing 25 μg/ml ampicillin (Sigma Co.), 0.25 mM IPTG (Wako Pure Chemicals) and 0.005% X-gal (Sigma Co.) using E. coli Y-1090 (acquired from Amersham Co.) as an indicator strain. After incubation at a temperature of 42° C. for 16 hours, about $7.4 \times 10^5$ of plaques were obtained and the plaques were used as library. With regard to the thus prepared library, survey was made with anti-N-acetylmannosamine dehydrogenase serum according to the method described in brochure (section 5, page 8) by Promega Biotec Co. to give recombinant bacteriophage λgtll-NAM 6 DNA having a part of the N-acetylmannosamine dehydrogenase gene.

(3) Preparation of recombinant plasmid pNAM 106 DNA and preparation of restriction enzyme cleavage map of recombinant plasmid pNAM 106 DNA After 2 μg of the DNA obtained by purifying the recombinant bacteriophage λgtll-NAM 6 DNA obtained in STEP (2) following the method described in Molecular Cloning, pages 371–372, Cold Spring Harbor Laboratory (1982) and 10 units of restriction enzyme EcoR I (manufactured by Takara Shuzo Co., Ltd.) were mixed with Tris-HCl buffer (pH 7.5) containing 10 mM $MgCl_2$, 1 mM dithiothreitol and 100 mM NaCl (hereafter abbreviated as H-buffer), the mixture was reacted at a temperature of 37° C. for 16 hours.

After the reaction was completed, the reaction solution was separated by 0.7% (W/V) agarose gel (manufactured by Takara Shuzo Co., Ltd.) electrophoresis. The gel portion containing 2.0 kbp of EcoR I-EcoR I DNA fragment in the recombinant bacteriophage λgtll-NAM 6 DNA was excised from the gel and the DNA was recovered by adsorption onto glass powder after dissolving the gel in NaI according to the method of DIA-IATRON DNA PREP obtained from Diatron K.K.

Then, 0.5 μg of plasmid pUC19 DNA (manufactured by Takara Shuzo Co., Ltd.) and 10 units of restriction enzyme EcoR I were mixed with H-buffer respectively. After reacting at a temperature of 37° C. for 2 hours, the reaction mixture was extracted with phenol and precipitated with ethanol in a conventional manner to give plasmid pUC19 DNA digested with EcoR I.

A mixture of 0.5 μg of 2.0 kbp EcoR I-EcoR I fragment of the recombinant bacteriophage λgtll-NAM 6 DNA thus obtained, 0.5 μg of plasmid pUC19 DNA digested with EcoR I and 1 unit of T4 DNA ligase (manufactured by Boehringer Mannheim Co.) was added to Tris-HCl buffer (pH 7.5) containing 66 mM $MgCl_2$, 10 mM dithiothreitol and 10 mM ATP. The mixture was reacted at a temperature of 16° C. for 16 hours to ligate DNA. Using the reaction solution, E. coli JM 109 strain (acquired from Takara Shuzo Co., Ltd.) was transformed with this reaction solution, according to the method of D. M. Morrison [Methods in Enzymology, 68, 326–331 (1979)]. The transformants were surveyed in terms of chemical resistance (ampicillin resistance) and β-galactosidase activity. The recombinant plasmid contained in the desired transformant thus obtained was named pNAM 106.

E. coli JM 109 (pNAM 106) was cultured in medium composed of 1% (W/V) Trypton, 0.5% (W/V) yeast extract and 0.5% (W/V) NaCl at a temperature of 37° C. for 16 hours. The culture solution, 20 ml, was inoculated on 1 liter of the medium. After shake culture at a temperature of 37° C. for 3 hours, 0.2 g of chloramphenicol was added to the culture solution. Incubation was continued for further 20 hours at the same temperature to give the culture solution.

Then, the culture solution was centrifuged at 10,000 rpm for 10 minutes in a conventional manner to give wet cake. After the wet cake was suspended in 50 mM Tris-HCl (pH 8.0) containing 20 ml of 25% (W/V) sucrose, 10 mg of lysozyme, 8 ml of 0.25 M EDTA solution (pH 8.0) and 8 ml of 20% (w/v) sodium dodecylsulfate were added to the suspension, respectively. The mixture was kept at 60° C. for 30 minutes to cause lysis. The lysate was thus obtained.

To the lysate was added 13 ml of 5 M NaCl solution. The mixture was treated at 4° C. for 16 hours and then centrifuged at 15,000 rpm for 30 minutes in a conventional manner to give the extract. After extraction with phenol and then precipitation with ethanol in a conventional manner, the precipitates were obtained.

Then, the precipitates were subjected to a conventional drying treatment under reduced pressure, which was then dissolved in 6 ml of 10 mM Tris-HCl buffer (pH 7.5) containing 1 mM EDTA. After 6 g of cesium chloride and 0.2 ml of 10 mg/ml of ethidium bromide were added to the solution, the mixture was subjected to equilibrium density gradient centrifugation at 39,000 rpm for 42 hours using an ultra centrifugation machine to isolate recombinant plasmid pNAM 106 DNA. Ethidium bromide was then removed with n-butanol, and dialysis was performed to 10 mM Tris-HCl buffer containing 1 mM EDTA to give 800 μg of purified recombinant plasmid pNAM 106 DNA.

Figure 1:
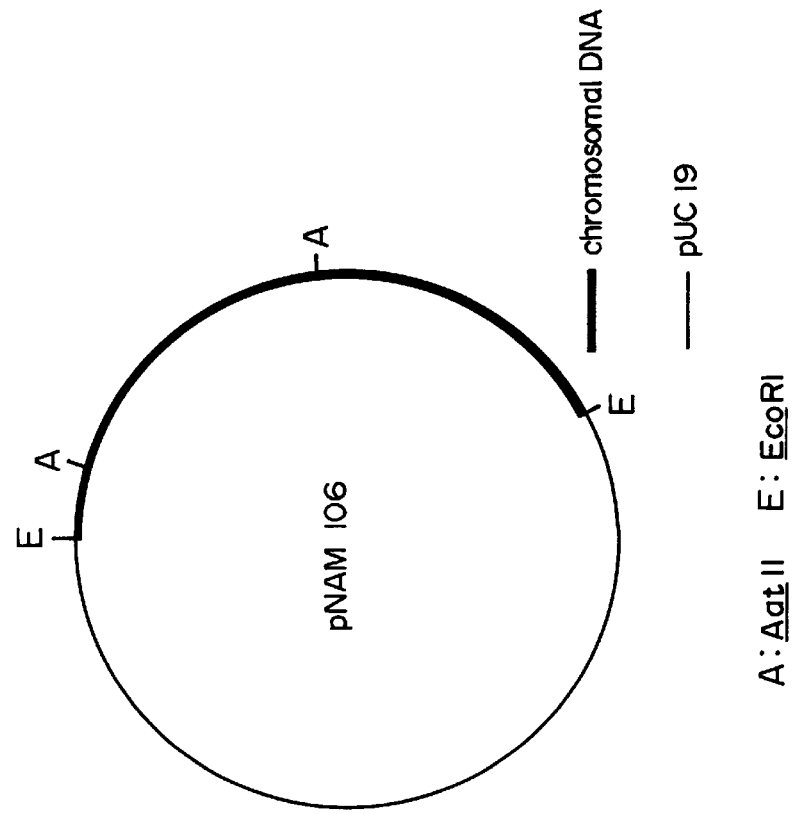
FIG. 1 shows a restriction enzyme cleavage map of recombinant plasmid PNAM 106 DNA.

The recombinant plasmid pNAM 106 DNA was subjected to single digestion and double digestion with restriction enzymes Aat II and EcoR I (both manufactured by Takara Shuzo Co., Ltd.). Mobility of the resulting DNA fragments was analyzed by agarose gel electrophoresis. The thus obtained mobility patterns were contrasted to the standard mobility patterns of the DNA fragment obtained by digestion of bacteriophage ADNA (manufactured by Takara Shuzo Co., Ltd.) with Hind III to prepare a restriction enzyme map. The map is shown in FIG. 1.

(4) Preparation of recombinant plasmid pNAM 301 DNA

Following the procedures of STEP (1), chromosomal DNA of Flavobacterium sp. No. 141-8 strain was extracted, and 60 μg of this chromosomal DNA and 50 units of restriction enzyme Sau3 AI (manufactured by Takara Shuzo Co., Ltd.) were mixed with Tris-HCl buffer (pH 7.5) containing 10 mM $MgCl_2$, 1 mM dithiothreitol and 50 mM NaCl (hereafter abbreviated as M-buffer), respectively followed by reacting them at a temperature of 37° C. for an hour. After the reaction was completed, the reaction solution was extracted with phenol and precipitated with phenol in a conventional manner, agarose gel electrophoresis was carried out. By eluting by the method of R.C.A. Yang et al. described in STEP (2), the eluate was obtained. The eluate was extracted with phenol and precipitated with ethanol in a conventional manner to give 5 μg of chromosomal DNA fragment of Flavobacterium sp. No. 141-8 strain digested with Sau3 AI.

Next, 1 μg of the digestion product of EMBL 3 bacteriophage/vector DNA with BamH I [manufactured by STRATAGENE Co., Ltd.], 1 μg of the chromosomal DNA fragment of Flavobacterium sp. No. 141-8 strain digested with Sau3 AI obtained above and 2 units of T4 DNA ligase (manufactured by Boehringer Mannheim Co.) were added to 66 mM Tris-HCl buffer (pH 7.5) containing 66 mM $MgCl_2$, 10 mM dithiothreitol and 10 mM ATP. The mixture was reacted at 16° C. for 16 hours to ligate DNA.

Then, the DNA mixture was enclosed with enveloped protein of bacteriophage by the in vitro packaging method [Methods in Enzymology, 68, 281–298 (1979)] to prepare bacteriophage particles. The bacteriophage particles thus obtained were inoculated on Trypton agar medium [1% Trypton (manufactured by Difco Co.), 0.25% NaCl and 1.2% agar] using E. coli P2392 (acquired from STRATAGENE Co.) as an indicator strain. After incubation at a temperature of 37° C. for 16 hours, about 4000 plaques were obtained and the plaques were used as library.

After 2 μg of the recombinant plasmid pNAM 106 DNA obtained in STEP (3) and restriction enzyme Aat II (manufactured by Boehringer Mannheim Co., Ltd.) were mixed with M-buffer, the mixture was reacted at a temperature of 37° C. for 2 hours. After the reaction was completed, the reaction solution was separated by 0.7% (W/V) agarose gel electrophoresis. The gel portion containing 0.9 kbp of Aat II-Aat II DNA fragment in the recombinant plasmid PNAM 106 DNA was excised from the gel and the DNA was recovered by the method of DIA-IATRON DNA PREP. From 0.1 μg of the 0.9 kbp Aat II-Aat II DNA fragment obtained, radioactive probe was prepared by [$\alpha$-$P^{32}$] dCTP (purchased from Amersham Japan, 3000 ci/nmol) by Random Primer Extension Labeling System [manufactured by Du Pont Inc.].

Using this radioactive probe, plaque hybridization was performed with the library prepared with the aforesaid EMBL 3 phage vector, according to the method described in Current Protocols in Molecular Biology (John Wiley & Sons, Inc.). As the result, 4 positive clones were obtained. These recombinant phages were proliferated using E. coli LE392 (acquired from STRATAGENE Co.) as an indicator strain and the DNA was extracted by the method described in T. Maniatis et al., (1982) Molecular Cloning. The BamH I digestion products of these phage DNAs were subjected to 0.7% agarose gel electrophoresis and transferred onto a nitrocellulose filter. Then Southern blotting hybridization was carried out using the aforesaid radioactive probe prepared from the 0.9 kbp Aat II—Aat II DNA fragment, according to the method described in Current Protocols in Molecular Biology (John Wiley & Sons, Inc.). As the result, the BamH I-BamH I DNA fragment of 3.9 kb was hybridized with the probe in 4 strains in common. Therefore, the gel portion containing this 3.9 kb BamH I-BamH I DNA fragment was excised from the gel and the DNA was recovered by the method of DIA-IATRON DNA PREP.

Subsequently, 0.5 μg of plasmid pUC19 DNA (manufactured by Takara Shuzo Co., Ltd.) and 10 units of restriction enzyme BamH I were mixed with H-buffer respectively. After reacting at a temperature of 37° C. for 2 hours, the reaction mixture was extracted with phenol and precipitated with phenol in a conventional manner to give plasmid pUC19 DNA digested with BamH I. The 3.9 kb BamH I-BamH I DNA fragment, 0.5 μg, obtained as above was ligated with 0.5 μg of plasmid pUC19 DNA digested with BamH I according to the procedures described in STEP (3) to give recombinant plasmid PNAM 301 DNA. Furthermore, E. coli JM 109 (pNAM 301) was incubated by the procedures described in STEP (3) and the plasmid contained in this strain was purified to give 800 μg of purified recombinant plasmid pNAM 301 DNA.

The recombinant plasmid PNAM 301 DNA was subjected to single digestion and double digestion with restriction enzymes Aat II, BamH I, Bgl II, Sal I and Sph I (all manufactured by Takara Shuzo Co., Ltd.). Mobility pattern of the resulting DNA fragments was analyzed by agarose gel electrophoresis. The thus obtained mobility patterns were contrasted to the standard mobility patterns of the DNA fragment obtained by digestion of bacteriophage λDNA (manufactured by Takara Shuzo Co., Ltd.) with Hind III to prepare a restriction enzyme map. The map is shown in FIG. 2.

(5) Preparation of recombinant plasmid pNAM 305 DNA

After 2 μg of the recombinant plasmid pNAM 301 DNA obtained in STEP (4) and restriction enzymes BamH I and Bgl II (both manufactured by Takara Shuzo Co., Ltd.) were mixed with H-buffer, the mixture was reacted at a temperature of 37° C. for 2 hours. After the reaction was completed, the reaction solution was separated by 0.7% (W/V) agarose gel electrophoresis. The gel portion containing 2.4 kbp of BamH I-Bgl II DNA fragment in the recombinant plasmid pNAM 301 DNA was excised from the gel and 2 μg of the DNA was recovered by the method of DIA-IATRON DNA PREP.

Subsequently, 0.5 μg of plasmid pUC19 DNA (manufactured by Takara Shuzo Co., Ltd.) was digested with BamH I in a manner similar to STEP (4). The digestion product of this plasmid pUC19 DNA with BamH I was ligated with the 2.4 kg BamH I-Bgl II DNA fragment of the aforesaid recombinant plasmid pNAM 301 DNA according to the procedures described in STEP (3) to give recombinant plasmid pNAM 304 DNA. Furthermore, E. coli JM 109 (pNAM 304) was incubated by the procedures described in STEP (3) and the plasmid contained in this strain was purified to give 800 μg of purified recombinant plasmid pNAM 304 DNA.

The recombinant plasmid pNAM 304 DNA, 15 μg, obtained as described above and restriction enzymes Pst II and Xba I (both manufactured by Takara Shuzo Co., Ltd.) were mixed with H-buffer, respectively. After the mixture was reacted at a temperature of 37° C. for 2 hours, the reaction mixture was extracted with phenol and precipitated with ethanol to give pNAM 304 DNA digested with Pst II and Xba I. The thus obtained DNA was treated with Kilo Sequencing Kit (manufactured by Takara Shuzo Co., Ltd.), whereby DNA was deleted to give recombinant plasmid pNAM 305 DNA having the inserted fraction deleted by 0.4 kb from Xba I out of the inserted fragments of the recombinant plasmid PNAM 304 DNA.

Using recombinant plasmid pNAM 305 DNA, transformant E. coli JM 109 (pNAM 305) was transformed, according to the method of D. M. Morrison [Methods in Enzymology, 68, 326–331 (1979)] (the transformant has been deposited in the Fermentation Research Institute of the Agency of Industrial Science and Technology of Japan under FERM BP-2692) was shake cultured at 37° C. for 8 hours in 10 ml of T-Y medium [1% (W/V) Trypton, 0.5% (W/V) yeast extract and 0.5% (W/V) NaCl] containing 1 mM IPTG. The cells were then collected and homogenized with ultrasonic wave. The resulting crude enzyme solution showed an N-acetylmannosamine dehydrogenase activity of 0.12 U/ml. Surprisingly, this value was almost comparable to or better than that of Flavobacterium sp. No. 141-8 strain which required complicated incubation over a long period of time according to U.S. Ser No. 07/121,916 which is a co-pending prior application by the present inventors.

For the purpose of comparison, the activity of N-acetylmannosamine dehydrogenase obtained in a similar manner except for using E. coli JM 109 (acquired from Takara Shuzo Co., Ltd.) bearing plasmid pUC19 (manufactured by Takara Shuzo Co., Ltd.) was determined but no activity was noted.

(6) Analysis of nucleotide sequence of DNA containing N-acetylmannosamine dehydrogenase gene Sequencing of recombinant plasmid pNAM 305 was performed using Sequencing Kit (manufactured by Toyobo Co., Ltd.). Primer was synthesized using System 1 Plus DNA Synthesizer (manufactured by Beckmann Co.).

Gel electrophoresis for analysis of nucleotide sequence was performed using 8% (W/V) polyacrylamide gel (manufactured by Fuji Photo Film Co., Ltd.).

The entire nucleotide sequence of the N-acetylmannosamine dehydrogenase gene alone and the amino acid sequence of polypeptide translated from the gene are shown as SEQ ID NO:1 and SEQ ID NO:2, respectively.

What is claimed is:

1. An isolated polydeoxyribonucloetide comprising an N-acetylmannosamine dehydrogenase gene derived from a microorganism belonging to the genus Flavobacterium, which encodes a sequence of 271 amino acids (SEQ ID NO:2).

2. A DNA construct consisting of a vector containing an N-acetylmannosamine dehydrogenase gene derived from a microorganism belong to the genus Flavobacterium, wherein said N-acetylmannosamine dehydrogenase gene encodes a sequence of 271 amino acids (SEQ ID NO:2).

3. A method for production of N-acetylmannosamine dehydrogenase which comprises culturing in a medium a microorganism belonging to the genus Escherichia, containing recombinant DNA obtained by incorporating N-acetylmannosamine dehydrogenase gene derived from a microorganism belonging to the genus Flavobacterium, wherein said N-acetylmannosamine dehydrogenase gene encodes a sequence of 271 amino acids (SEQ ID NO:2).

4. A method for the production of N-acetyl mannosamine dehydrogenase which comprises culturing in a medium a microorganism of *E. coli* strain Y1090 containing recombinant DNA obtained by incorporating N-acetyl mannosamine dehydrogenase gene derived from Flavobacterium sp. No. 141-8 strain into pUC19, wherein said N-acetyl mannosamine dehydrogenase gene encodes a sequence of 271 amino acids (SEQ ID NO:2).

* * * * *

UNITED STATES PATENT AND TRADEMARK OFFICE
CERTIFICATE OF CORRECTION

PATENT NO.: 5,942,427

DATED: August 24, 1999

INVENTOR(S): Hideko OTAKE, *et al.*

It is certified that an error appears in the above-identified patent and that said Letters Patent is hereby corrected as shown below:

On the title page,
In item [56] References Cited:

U.S. Patent Document No. 4,768,592; Delete "9/1988" and insert --11/1988--.

In the Abstract:

--Novel recombinant DNA contains-- should be the first four words of the abstract.

Signed and Sealed this

Eighteenth Day of July, 2000

*Attest:*

Q. TODD DICKINSON

*Attesting Officer*    *Director of Patents and Trademarks*

SEQUENCE LISTING (1) GENERAL INFORMATION:

(iii) NUMBER OF SEQUENCES: 2

(2) INFORMATION FOR SEQ ID NO:1:

```
       (i) SEQUENCE CHARACTERISTICS:
           (A) LENGTH: 816 base pairs
           (B) TYPE: nucleic acid
           (C) STRANDEDNESS: single
           (D) TOPOLOGY: linear (ii) MOLECULE TYPE: DNA (genomic)

(vi) ORIGINAL SOURCE:
           (A) ORGANISM: Flavobacterium
           (B) STRAIN: Flavobacterium sp. No. 141-8

(ix) FEATURE:
           (A) NAME/KEY: CDS
           (B) LOCATION: 1..813
           (D) OTHER INFORMATION:

(xi) SEQUENCE DESCRIPTION: SEQ ID NO:1:

ATG ACG ACA GCA GGC GTT TCG AGG CGG CCC GGA CGG CTT GCG GGC AAG        48
Met Thr Thr Ala Gly Val Ser Arg Arg Pro Gly Arg Leu Ala Gly Lys
 1               5                  10                  15

GCG GCG ATC GTC ACC GGC GCC GCC GGC GGC ATC GGC CGC GCC ACC GTC        96
Ala Ala Ile Val Thr Gly Ala Ala Gly Gly Ile Gly Arg Ala Thr Val
                20                  25                  30

GAG GCC TAT CTT CGC GAG GGC GCC AGC GTG GTG GCG ATG GAC CTC GCG       144
Glu Ala Tyr Leu Arg Glu Gly Ala Ser Val Val Ala Met Asp Leu Ala
            35                  40                  45

CCG CGC CTC GCC GCG ACC CGC TAC GAG GAA CCC GGC GCC ATC CCG ATC       192
Pro Arg Leu Ala Ala Thr Arg Tyr Glu Glu Pro Gly Ala Ile Pro Ile
        50                  55                  60

GCC TGC GAC CTT GCC GAC CGC GCC GCG ATC GAC GCG GCG ATG GCC GAC       240
Ala Cys Asp Leu Ala Asp Arg Ala Ala Ile Asp Ala Ala Met Ala Asp
 65                 70                  75                  80

GCG GTC GCC CGC CTC GGC GGG CTG GAC ATT CTC GTC GCC GGC GGC GCG       288
Ala Val Ala Arg Leu Gly Gly Leu Asp Ile Leu Val Ala Gly Gly Ala
                85                  90                  95

CTC AAG GGC GGC ACC GGC AAT TTC CTC GAT CTC TCC GAC GCC GAC TGG       336
Leu Lys Gly Gly Thr Gly Asn Phe Leu Asp Leu Ser Asp Ala Asp Trp
            100                 105                 110

GAC CGC TAT GTC GAC GTC AAC ATG ACC GGC ACC TTC CTC ACC TGC CGC       384
Asp Arg Tyr Val Asp Val Asn Met Thr Gly Thr Phe Leu Thr Cys Arg
        115                 120                 125

GCC GGC GCC CGC GCC ATG GTG GCG GCC GGC GCC GGC AAG GAC GGC CGG       432
Ala Gly Ala Arg Ala Met Val Ala Ala Gly Ala Gly Lys Asp Gly Arg
130                 135                 140

TCC GCG CGC ATC ATC ACC ATC GGC TCC GTC AAT TCC TTC ATG GCC GAG       480
Ser Ala Arg Ile Ile Thr Ile Gly Ser Val Asn Ser Phe Met Ala Glu
145                 150                 155                 160

CCG GAG GCG GCC GCC TAT GTC GCG GCC AAG GGC GGC GTC GCC ATG CTG       528
Pro Glu Ala Ala Ala Tyr Val Ala Ala Lys Gly Gly Val Ala Met Leu
                165                 170                 175

ACC CGC GCC ATG GCC GTC GAC CTC GCC CGC CAC GGC ATC CTC GTC AAC       576
Thr Arg Ala Met Ala Val Asp Leu Ala Arg His Gly Ile Leu Val Asn
            180                 185                 190

ATG ATT GCC CCC GGC CCC GTC GAC GTG ACC GGC AAC AAC ACC GGC TAC       624
Met Ile Ala Pro Gly Pro Val Asp Val Thr Gly Asn Asn Thr Gly Tyr
        195                 200                 205

AGC GAA CCG CGC CTC GCC GAG CAG GTC CTC GAC GAG GTG GCG CTG GGC       672
Ser Glu Pro Arg Leu Ala Glu Gln Val Leu Asp Glu Val Ala Leu Gly
210                 215                 220

AGG CCC GGC CTG CCG GAG GAA GTG GCG ACC GCC GCG GTC TTC CTG GCC       720
Arg Pro Gly Leu Pro Glu Glu Val Ala Thr Ala Ala Val Phe Leu Ala
225                 230                 235                 240

GAG GAC GGG TCG AGC TTC ATC ACC GGC TCG ACG ATC ACC ATC GAC GGC       768
```

```
Glu Asp Gly Ser Ser Phe Ile Thr Gly Ser Thr Ile Thr Ile Asp Gly
                245                 250                 255

GGC CTC TCC GCC ATG ATC TTC GGC GGC ATG CGG GAA GGC CGA CGC        813
Gly Leu Ser Ala Met Ile Phe Gly Gly Met Arg Glu Gly Arg Arg
                260                 265                 270

TGA                                                                816
```

(2) INFORMATION FOR SEQ ID NO:2:

(i) SEQUENCE CHARACTERISTICS:
        (A) LENGTH: 271 amino acids
        (B) TYPE: amino acid
        (D) TOPOLOGY: linear (ii) MOLECULE TYPE: protein (xi) SEQUENCE DESCRIPTION: SEQ ID NO:2:

```
Met Thr Thr Ala Gly Val Ser Arg Arg Pro Gly Arg Leu Ala Gly Lys
 1               5                  10                  15

Ala Ala Ile Val Thr Gly Ala Ala Gly Gly Ile Gly Arg Ala Thr Val
                20                  25                  30

Glu Ala Tyr Leu Arg Glu Gly Ala Ser Val Val Ala Met Asp Leu Ala
                35                  40                  45

Pro Arg Leu Ala Ala Thr Arg Tyr Glu Glu Pro Gly Ala Ile Pro Ile
    50                  55                  60

Ala Cys Asp Leu Ala Asp Arg Ala Ala Ile Asp Ala Ala Met Ala Asp
65                  70                  75                  80

Ala Val Ala Arg Leu Gly Gly Leu Asp Ile Leu Val Ala Gly Gly Ala
                85                  90                  95

Leu Lys Gly Gly Thr Gly Asn Phe Leu Asp Leu Ser Asp Ala Asp Trp
                100                 105                 110

Asp Arg Tyr Val Asp Val Asn Met Thr Gly Thr Phe Leu Thr Cys Arg
                115                 120                 125

Ala Gly Ala Arg Ala Met Val Ala Ala Gly Ala Gly Lys Asp Gly Arg
                130                 135                 140

Ser Ala Arg Ile Ile Thr Ile Gly Ser Val Asn Ser Phe Met Ala Glu
145                 150                 155                 160

Pro Glu Ala Ala Ala Tyr Val Ala Ala Lys Gly Gly Val Ala Met Leu
                165                 170                 175

Thr Arg Ala Met Ala Val Asp Leu Ala Arg His Gly Ile Leu Val Asn
                180                 185                 190

Met Ile Ala Pro Gly Pro Val Asp Val Thr Gly Asn Asn Thr Gly Tyr
                195                 200                 205

Ser Glu Pro Arg Leu Ala Glu Gln Val Leu Asp Glu Val Ala Leu Gly
                210                 215                 220

Arg Pro Gly Leu Pro Glu Glu Val Ala Thr Ala Ala Val Phe Leu Ala
225                 230                 235                 240

Glu Asp Gly Ser Ser Phe Ile Thr Gly Ser Thr Ile Thr Ile Asp Gly
                245                 250                 255

Gly Leu Ser Ala Met Ile Phe Gly Gly Met Arg Glu Gly Arg Arg
                260                 265                 270
```